US010463796B2

(12) United States Patent
Thorne (10) Patent No.: US 10,463,796 B2
(45) Date of Patent: Nov. 5, 2019

(54) ASYMMETRIC MALE VALVES FOR TAPERED FEMALE FITTINGS

(71) Applicant: Gale Harrison Thorne, Bountiful, UT (US)

(72) Inventor: Gale Harrison Thorne, Bountiful, UT (US)

(73) Assignee: THORNE MEDICAL, LLC, Bountiful, UT (US)

( * ) Notice: Subject to any disclaimer, the term of this patent is extended or adjusted under 35 U.S.C. 154(b) by 229 days.

(21) Appl. No.: 15/732,047

(22) Filed: Sep. 9, 2017

(65) Prior Publication Data

US 2018/0056005 A1  Mar. 1, 2018

Related U.S. Application Data

(63) Continuation-in-part of application No. 15/530,257, filed on Dec. 15, 2016, now abandoned, which is a
(Continued)

(51) Int. Cl.
*A61M 5/31* (2006.01)
*A61M 39/26* (2006.01)
(Continued)

(52) U.S. Cl.
CPC ............. *A61M 5/31* (2013.01); *A61M 5/002* (2013.01); *A61M 5/19* (2013.01); *A61M 5/3129* (2013.01);
(Continued)

(58) Field of Classification Search
CPC .. A61M 2005/3106; A61M 2005/3103; A61M 2005/3128; A61M 2039/2426;
(Continued)

(56) References Cited

U.S. PATENT DOCUMENTS

1,742,497 A * 1/1930 Dickinson ............. A61M 5/344
604/242
4,874,377 A * 10/1989 Newgard ............ A61M 39/045
604/167.02
(Continued)

*Primary Examiner* — William R Carpenter
(74) *Attorney, Agent, or Firm* — Gale H. Thorne (57) ABSTRACT

Two embodiments of a normally closed asymmetric tapered fitting valve are disclosed. Each tapered fitting valve comprises a single molded incompressible, but supple part and a skeletal support whereby the tapered fitting valve is opened by insertion into a correspondingly sized female tapered fitting. Use of the valve specifically targets use with medical luer fittings, but is not limited thereto. The preferred embodiment of an actuator portion of the valve has dimensions which are identical those of a female tapered fitting into which the valve is inserted to open. The valve opens by compressing a slit which is disposed along a major axis of the asymmetric valve as it is advanced through a tapered circular duct. The valve has back-to-back closure features which maintain the valve closed when not inserted. A stand-alone male adapter comprising the tapered fitting valve is disclosed. Also, a syringe barrel comprising a skeletal support structure for a securely affixed valve to thereby provide a syringe barrel with an integrally affixed male adapter is also disclosed.

7 Claims, 5 Drawing Sheets

Related U.S. Application Data continuation-in-part of application No. 14/921,343, filed on Oct. 23, 2015, now Pat. No. 9,950,114, which is a continuation-in-part of application No. 14/121,681, filed on Oct. 7, 2014, now abandoned, which is a continuation-in-part of application No. 13/872,828, filed on Apr. 29, 2013, now Pat. No. 9,295,827.

(51) Int. Cl.

| | | |
|---|---|---|
| *A61M 39/10* | (2006.01) | |
| *A61M 5/00* | (2006.01) | |
| *A61M 5/19* | (2006.01) | |
| *A61M 5/315* | (2006.01) | |
| *A61M 5/36* | (2006.01) | |
| *A61M 5/50* | (2006.01) | |
| *A61M 5/178* | (2006.01) | |
| *A61M 39/24* | (2006.01) | |

(52) U.S. Cl.
CPC .... *A61M 5/31501* (2013.01); *A61M 5/31511* (2013.01); *A61M 5/31596* (2013.01); *A61M 5/365* (2013.01); *A61M 5/5086* (2013.01); *A61M 39/10* (2013.01); *A61M 39/26* (2013.01); *A61M 2005/1787* (2013.01); *A61M 2005/3114* (2013.01); *A61M 2005/3121* (2013.01); *A61M 2005/3125* (2013.01); *A61M 2005/3128* (2013.01); *A61M 2039/1033* (2013.01); *A61M 2039/2426* (2013.01)

(58) Field of Classification Search
CPC .... A61M 2039/2433; A61M 2039/604; A61M 2039/0646
See application file for complete search history.

(56) References Cited

U.S. PATENT DOCUMENTS

| | | | | |
|---|---|---|---|---|
| 5,061,253 | A * | 10/1991 | Yoshida | A61M 39/26 251/342 |
| 5,807,348 | A * | 9/1998 | Zinger | A61M 39/045 604/246 |
| 9,295,827 | B2 * | 3/2016 | Thorne | A61M 39/24 |
| 9,950,114 | B2 * | 4/2018 | Thorne, Jr. | A61M 5/31596 |
| 2004/0158208 | A1 * | 8/2004 | Hiejima | A61M 39/0606 604/167.04 |
| 2009/0287154 | A1 * | 11/2009 | Harding | A61M 39/0606 604/167.04 |
| 2015/0032063 | A1 * | 1/2015 | Thorne | A61M 5/31596 604/207 |
| 2016/0175537 | A1 * | 6/2016 | Thorne, Jr. | A61M 5/31596 604/111 |

* cited by examiner

ASYMMETRIC MALE VALVES FOR TAPERED FEMALE FITTINGS

CONTINUITY

This application is a Continuation-in-Part of U.S. patent application Ser. No. 15/530,257, filed Dec. 15, 2016 and titled ISO COMPLIANT MALE LUER TAPERED VALVES (referenced hereafter as Thorne 257) which is a Continuation-in-Part of U.S. patent application Ser. No. 14/921,343 filed Oct. 23, 2015 and titled DUAL-CHAMBER SYRINGE AND ASSOCIATED CONNECTING SYSTEMS by Gale H. Thorne, Jr., et al., which is a Continuation-in-Part of U.S. patent application Ser. No.: 14/121,681 filed Oct. 7, 2014 and titled COMPONENTS AND DEVICES FOR CLOSED MEDICAL SYSTEM OPERATION by Gale H. Thorne which is a Continuation-in-Part of U.S. patent application Ser. No. 13/872,828, filed Apr. 29, 2013 and titled TWISTED SLIT VALVE filed by Gale H. Thorne, now on record as U.S. Pat. No. 9,295,827 B2, allowed Mar. 29, 2016. In particular, contents of Thorne 257 are made part hereof, by this reference.

FIELD OF INVENTION

This application relates to tapered fitting connectors which employ self-closing valves, in general, and to normally-closed male valves opened by insertion into tapered female fittings, in particular, such valves being opened by compressive forces about the exterior of the valve and, once compressive force is removed, be self closing to stop fluid flow. Inventions disclosed within this application also relate, generally, to applications of such valves in male luer adapters for needleless interconnections, male luer replacement by such valves in otherwise conventional syringes. As such luer valves may be used internationally and be regulated by ISO 594-1 which stipulates that a male luer fitting should not exceed 0.0158 inches in diameter at the insertion end.

BACKGROUND AND DESCRIPTION OF RELATED ART

While the present invention broadly applies to self-closing valves which are opened by insertion into tapered fittings, it has particular application to self-sealing male and female luer valves used, for example, in the following medical applications.

Example 1: Male Adapter Valves

Two primary prior art patents well disclose the need and opportunity for a male luer valve which is opened upon insertion into a female luer fitting. The first, U.S. Pat. No. 7,766,304 B2 issued to John C. Phillips (Phillips 304) Aug. 3, 2010 and titled, SELF-SEALING MALE LUER CONNECTOR WITH BIASED VALVE PLUG discloses a male luer connector for connection with a female luer connector. Phillips 304 further discloses a device comprising a tubular male body and a surrounding displaceable cuff. A valve plug is slidably disposed within the housing and formed to, in a first state, seal a communicating hole and, in a second state, be displaced to open the hole for fluid communication. Closure is biased to occur by an elastomeric coupling which communicates with the plug.

The second, U.S. Pat. No. 7,803,140 B2 issued to Thomas F. Fangrow, et al (Fangrow 140) Aug. 16, 2011 and titled, MEDICAL CONNECTOR discloses two primary designs for a male luer connector for connection with a female luer connector. The first design comprises a plugging component which is offset to open a valve for fluid flow. The second design discloses a slit valve which is opened for flow by insertion of a piercing part.

Such male valves provide barriers for infecting bacteria and debris, but perhaps more importantly provide a self-closing barrier and, thus, a closed system against inadvertent leakage, wherein product associated with such leakage might be a hazardous drug. It is important to note that such male valves should only be disposed in an open state while the valve is inserted into a complementary female fitting. At this date, all contemporary commercial male adapters known to the inventor for needleless connectors employ either a linear displacement mechanism which removes a "plug" from a hole when the valve is inserted into a female luer fitting or a forced open slit. Such mechanisms are commonly complex in structure and, therefore, result in an elevated component cost. Generally within the scope and meaning of this Application, the term male luer adapter shall be used as a reference for such needleless connector devices.

Further, male luer adapters such as those provided as examples, supra, are actuated to an open state by either a displacement of a plug within a hole or by a slit of a valve being parted by insertion of a piercing part. In the case of plug displacement, such is known to often result in a small droplet of liquid remaining resident at the exterior of the hole and plug site upon closure.

Example 2: Luer Fitting Replacements on Otherwise Conventional Medical Syringes The value of adding a male adapter fitting to a conventional medical syringe has been demonstrated by at least one company which currently sells one of the above cited male adapters by securely affixing a currently commercially available male adapter to a syringe and selling the combination as an integrated product. As is well understood in medical syringe art, definite advantages in cost and elimination of dead space would result by replacing a male luer fitting on a syringe with a male luer adapter made according to the present invention.

Within the scope of this application, terms which are absolute, such as round and unreactive, are understood to be permissive of manufacturing and physical limitations which, while functionally achieving a desired function, do not absolutely comply with definition of each specific term.

The following table provides a list of terms and associated definitions for words and phrases used herein.

assembly n: a device which is made from at least two interconnected parts barrel n: a cylindrical elongated portion of a conventional syringe which is substantially of constant diameter along a long axis of the syringe, open on one end to receive a plunger tip and plunger rod assembly used for displacing fluid within the barrel and partially closed at an opposite end except for an orifice or portal through which fluid is ejected or aspirated conventional adj: sanctioned by general custom; i.e. commonplace, ordinary disparate n: when used to describe a first volume of contents relative to another volume of contents, the first volume of contents being kept distinctly separate from the other volume of contents distal adj: a term which depicts placement away from a reference point (e.g. away from a user of a syringe)

downstream adj: a direction which is consistent with flow out of a syringe or away from a user fluid n: a substance (e.g. a liquid or gas) which tends to take the shape of a container front adj/n: when referenced to a syringe, distally disposed or a distally disposed site (e.g. a front of a syringe comprises the commonly provided luer fitting and associated orifice)

gas n: a fluid which is neither solid nor liquid liquid n: a fluid which is neither solid nor gaseous, free flowing like water medial adj: occurring away from an outer edge; disposed near the center of (e.g. disposed away from an edge or periphery and in the vicinity of a center of gravity or axis of symmetry)

proximal adj: opposite of distal (e.g. a term which depicts placement nearer to a reference point)

state n: a mode or condition of matter, e.g. gaseous, liquid or solid or of a device, such as an open state of a valve substantially adv: to a most reasonably achievable amount syringe n: a medical device used for injecting or withdrawing fluids, a syringe usually comprising a plunger and plunger rod disposed to be displaced within a conventional cylindrical syringe barrel and, for a dual-chamber syringe, includes a plunger valve to provide a dual-chamber syringe Table 1: Definitions for Terms Used

BRIEF SUMMARY AND OBJECTS OF THE INVENTION

In brief summary, this novel invention, while having broader applications, alleviates known problems related to providing a normally closed male tapered fitting valve which is opened when a portion of the valve is inserted into a tapered female luer fitting. Basic to the instant invention is a valve body having asymmetrical cross sectional dimensions formed about a planar slit. The valve body is preferably shaped and sized to conform with the width of the slit providing a predetermined, substantially constant wall thickness from slit to the outer surface of the valve body for device stability and reliability. The valve body is preferably made from a compliant, incompressible material having memory which, when not inserted, reforms to and maintains an unconstrained body in its originally formed (e.g. molded) state.

Within the valve body is a normally closed slit providing a valve formed with front-to-back controlled closure about both ends of the slit which provides a common fluid pathway when the valve is opened. The front-to-back closure control, being on opposite ends of the slit, form a normally closed single valve pathway when uninserted. Generally, the body, being asymmetric, is sized and shaped to reform by compression to fit snugly into a tapered female fitting to, thereby, compressively distort the valve body and open a valve pathway when inserted therein. As the valve body is compliant, a rigid insertion support is required when the body is being inserted into a tapered fitting. Of course, for medical applications, valve material must also be unreactive to physiological fluids. Such a material is butyl rubber which is used in contemporary syringe plunger applications for the valve body and polypropylene for the insertion support.

In Thorne 828, a twisted slit valve is disclosed. Efficacious operation of the twisted slit valve (i.e. closure to fluid flow upon removal from a tapered female fitting) is highly dependent upon valve slit closure due to twisted geometry and molded material interlinking. The instant invention disclosed herein is free from such constraints by providing valve geometry which is designed to be inherently closed, similar to "duck bill" valve design, when not actuated.

For the case of this instant invention, a pair of normally closed valve lips are preferably formed within that portion of a device which is inserted into a tapered female fitting. Duckbill valves are particularly well adapted for such purposes although a conventional duckbill valve will not meet requirements of a bidirectional bather. Commonly a duckbill valve has a pair of lips which are closed from a higher pressure differential imposed from a downstream direction, but open due to pressure exerted in an opposite direction. Providing a duckbill valve having opposition to flow in opposite directions assures valve closure unless the geometry of valve lips are physically (compressively) compromised to open a common communicating pathway.

For a valve which is opened by insertion into a tapered female fitting to operate efficaciously, a number of specific constraints must be met. One of the major constraints is associated with circumference compliance. At the distance where the device is fully inserted into an associated female fitting, the outer surface of the inserted device should have the same (sealing) circumference as the internal surface of the tapered female fitting along its insertion length. Also, for compressive forces to accomplish an effective seal, cross sectional area of the inserted fitting plus area of a predefined open fluid communicating pathway should be equal to the internal cross sectional area of the female tapered fitting along the insertion length. For such a combination to be effective, the fitting, before being inserted, must be noncircular (asymmetric) yet have the geometric dimensional characteristics disclosed supra.

For small valves, such as valves for luer fittings, dimensional constraints are challenging. To slit a valve while assuring tight maintenance of valve part accuracy, a careful technique for valve production and slitting is highly recommended. As an example, inner diameter of a female luer fitting is nominally less than 0.2 inches and lips of a slit valve may need to be less than 0.02 inches thick. Such slitting is common in making contemporary duck bill valves. Also, it is preferred that a wall about the slit be as uniform as possible because thinning in such devices leads to local wall weakness making device failure, due to high internal pressure, more likely.

Similar to the twisted valve of Thorne 828, valve opening may be accomplished in either of two modes. The first mode is by compressive distortion of the body to deform the slit from a closed planar state to a hollow cylindrical state, thereby creating an open fluid pathway. As the slit is preferably disposed along a common, medical plane within the valve, a hollow tubular cannula can be displaced through the planar pathway to provide a path for fluid flow, thereby changing the valve to an open state. Note, that, in either case, restructuring the body from a compressed state or removing the hollow tubular object should result in automatic lip and, therefore, valve closure.

In summary, in the case of valve opening by compressive valve body distortion, the exterior surface circumference of each body crosscut segment about the slit can be formed to have a predetermined dimension. Likewise, the dimensions of each valve body crosscut asymmetrical segment will have a predetermined length and width, dependent upon slit length upon which a crosscut circumference conforms. As stated supra, the valve body should be designed such that the crosscut circumference is equal along its length to the associated interior surface circumference of a hollow tapered tube (e.g. a female luer fitting) in which the valve is displaced for opening. Similarly, associated cross sectional areas of each fitting and valve should be equal.

In general, a valve device body (e.g. of a male luer adapter), according to the instant invention, has two ends. At the first end, comprising the slit, an asymmetric valve is formed to be used as a fitting element of a tapered connector. The second end comprises a means for forming a communicating, connecting part whereby fluid may be displaced through the valve. If, for example, the slit valve is part of a stand alone male luer adapter, such as those used in common medical applications, the first end would serve as a male luer fitting while at the second end, the body may be formed to communicate with a female luer fitting having a portion which is attachable to a fluid source implement.

In addition to being used within a stand-alone male luer adapter, using such an asymmetrically formed slit valve as a replacement for a male luer fitting of a syringe provides a basis for closed valve operation in a plurality of medical syringe applications. Such a replacement can provide a syringe which has a closed fluid delivery orifice within a valve support structure. As such, access to contents of the syringe is denied until the valve is compressively opened by, for example, being displaced into a female luer fitting.

For an internally disposed valve to be forced closed when not inserted, it is well known in the duck bill valve art to apply pressure upon the exterior of the lips about the slit while relying on the material matrix from which the valve is made to resume a closed state. Such is abetted in the instant invention to obviate proximally disposed dispensing flow by one or more dead-ended cavities disposed about valve lips. Such cavities are formed by displacement of a cylindrical insertion support into the second end to open blind slits disposed in the proximal end of the valve in the body. Pressure in each such cavity applies closing force upon lips of the interior valve to act against dispensing flow.

A previous application, from which this Patent Application Continues-in-Part, disclosed a molded cavity disposed adjacent a proximal portion of a through slit (main slit) which is opened to provide a communicating pathway. It has been found that compressive distortion of such a molded cavity, especially in a valve having an offset slit, distorts cavity boundaries which are then directed toward the main slit to deter that slit from opening. Also, due to molded cavity dimension requirements, it was found desirable, as disclosed in Thorne 257, to offset the main slit from the medial axis of the valve. Such an offset is undesirable due to a natural reduction in wall thickness.

In the instant invention, offsetting the main slit is not required. Elimination of offsetting provides much needed space for providing superiorly and inferiorly disposed blind slits in line with the main slit. By distorting material about the blind slits, a pair of blind cavities are formed as a consequence of interface with an appropriately formed insert support, as disclosed hereafter. However, providing such blind cavities does require additional slitting. Sensitive to maintaining a closed valve against increasing upstream pressure internal to the valve, slit closure can be abetted by communicating the internal valve upstream pressure along the most proximal plane of the slit. In such a case, a pathway is provided by molding grooves to form a channel in the face of the insert support. Within the channel, fluid communicated from an upstream pressurized source is directed radially outward about the plane of the slit. Such directed pressure causes expansion to stretch the body along the slit plane and thereby force the slits more tightly closed. In addition, pressure of fluid flowing into cavities formed by support distortion about the blind slits further acts to keep valve lips closed.

Another novel and important difference between disclosures of U.S. Patent Applications from which this instant invention continues are formation of a distal end of the valve which is sized and shaped to meet ISO standards and a tapered, asymmetric skirt which forms the proximal end of the valve.

Entry dimensions of a male luer insert are limited by ISO standards to dimensions which cannot be met directly by an asymmetric valve which must be compressively distorted to an open state in a female luer fitting. For this reason, a diminished front surface area of the valve is provided. In this embodiment, a transition section from the diminished area to the asymmetric body of the valve comprises linear translation dimensions which maintain compliant circumferential dimensions of a female luer fitting into which the valve is inserted to open.

A tapered asymmetrical skirt of the valve body provides a linear continuation of exterior valve taper throughout the length of the body. The skirt is preferably designed to extend proximally with the same exterior circumferential dimensions and taper as a female luer fitting into which the valve is displaced for opening. The skirt also preferably has a constant skin thickness and is sized and shaped to extend linearly, following a constant taper, from the valve to a retaining ring at the body's proximal end.

The inner surface of the skirt has circumferential dimensions which are the same as a round, tapered cylindrical insertion support which, as disclosed supra, is affixed into the valve skirt for valve rigidity and for defining a fluid sealing, circular female surface contact with a female luer fitting. The cylindrical insertion support comprises a through hole which provides fluid communication from an upstream fluid source and may be a part of a male adapter or of a syringe barrel as disclosed hereafter. For this purpose, the insertion support comprises a tapered cylindrical shape having the same circumferential dimensions as corresponding inner surface circumferences of the skirt.

At the interface where the insertion support and proximal end of the valve meet, the smaller or minor axis of the asymmetric valve is understandably smaller than the radius of the circular support. Upon support insertion, the skirt is distorted to correspond with the insertion support radius. This distortion results in opening the blind slits disclosed supra.

Such distortion could also provide forces which would act upon the valve slit to force the valve slit open. Such is alleviated by sizing the width (slit length) of the blind slits to conform with the main slit pathway width and by providing a fillet on the distal surface of the insertion support which reduces the effect of opposing dimensions at the interface.

Grooves in the intersecting plane of the insertion support, about the proximal plane of the main slit, provide the pathways for fluid pressure communication as disclosed supra. As mentioned supra side directed flow when acted upon by increased pressure tends to expand the valve body in the plane of the valve lips and thereby draws lips of the valve together to aid in valve lip closure maintenance as well as providing pressure in associated closed cavities which also acts to keeps lips closed.

Accordingly, it is a primary object to provide a normally closed asymmetric, tapered fitting valve which is made from a material which is substantially incompressible, elastic and deformable to be compressively opened when displaced into an elongated, tapered tube having an inside diameter which conformably deforms the valve to open a fluid pathway along a medially disposed slit.

It is a very important object to provide a normally closed asymmetric, tapered fitting valve comprising a single molded part of incompressible, elastic material which can be affixed as a male luer fitting and opened by displacement into a female luer fitting It is equally as important to provide an asymmetric, tapered fitting valve for a luer fitting which complies with ISO specifications.

It is an important object to provide a normally asymmetric, tapered closed and self-sealing slit valve which has two distinct and independent opening modes (i.e. by displacement into a hollow tapered tube of predetermined internal surface circumference and by displacement of a blunt cannula through the valve).

It is an object to provide an asymmetric, tapered fitting valve which is displaced to an open state by application of a medially directed force causing compressive deformation when displaced into a circular, tapered fitting.

It is another object to provide a self-sealing asymmetric, tapered fitting valve having a valve core which is molded from an incompressible, flexible and compliant material which returns to a stable closed state when removed from compression resulting from insertion into a tapered fitting.

It is an object to provide a method for making a common pathway through a slit valve which has two opposing normally closed ends within a single molded asymmetric, tapered fitting valve core.

It is a fundamental object to provide a tapered fitting valve which comprises a substantially constant wall thickness about a fluid communicating through hole when disposed in an open state.

It is a critical object to provide an asymmetric, tapered fitting valve having proximal skirt construction which has the same asymmetrical characteristic and taper as the valve.

It is an object to provide a stand-alone male luer adapter device which employs the tapered fitting valve.

It is another object to provide a normally closed valve which is formed to be an integral part of a medical syringe barrel which is opened by insertion into a female luer fitting.

It is an important object to provide a medical syringe which is closed by an asymmetric valve integrally affixed to a barrel of the syringe and only opened for fluid flow therefrom by compressive insertion of an integral valved male luer fitting into a female luer fitting.

It is a primary object to provide an asymmetric, tapered fitting male valve which can be used with conventional luer fittings and associated medical syringes.

It is a meaningful object to provide a syringe barrel which comprises a skeletal insertion support for an asymmetric, tapered fitting valve which replaces a male luer fitting conventionally disposed on a syringe such that an insertion support of the syringe barrel and associated valve part provide a male luer fitting which only opens when disposed within a female luer fitting.

These and other objects and features of the present invention will be apparent from the detailed description taken with reference to accompanying drawings.

DETAILED DESCRIPTION OF THE ILLUSTRATED EMBODIMENTS

While the instant inventions disclosed herein are applicable to a wide variety of tapered male/female insertion type fluid connectors, the detailed description provided herein is focused upon examples for medical devices. Reference is now made to the embodiments illustrated in FIGS. 1-15A wherein like numerals are used to designate like parts throughout and primes of numbers generally indicate parts which are similar in shape and/or function of those numbers, but not exactly the same.

Valve Part 10

Figure 1:
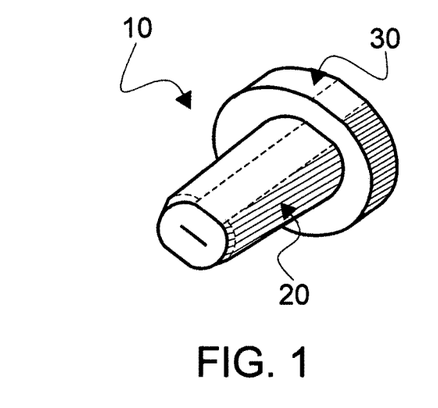
FIG. 1 is a perspective of a preferred embodiment of an asymmetric valve part which is parted to compressively open a valve pathway according to the instant invention, the valve part being preferably molded from incompressible, elastic material.
Figure 1A:
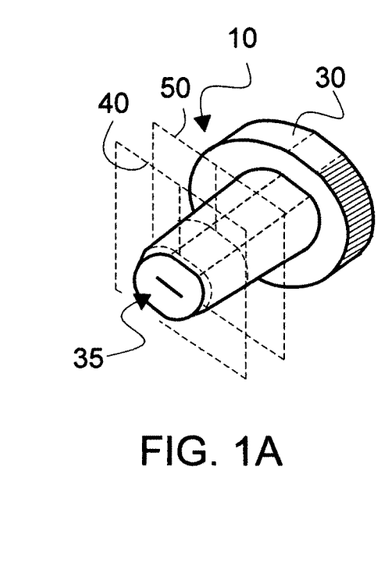
FIG. 1A is the perspective of the valve part seen in FIG. 1 with shading removed for a clearer view of planes disposed to identify crosscuts of the valve part at predetermined sites.

Reference is now made to FIGS. 1 and 1A wherein an asymmetric valve part 10 is seen. As seen in FIG. 1, valve part 10 comprises two sections, an asymmetric, tapered body 20 and a proximally disposed asymmetric anchor ring 30.

Figure 7:
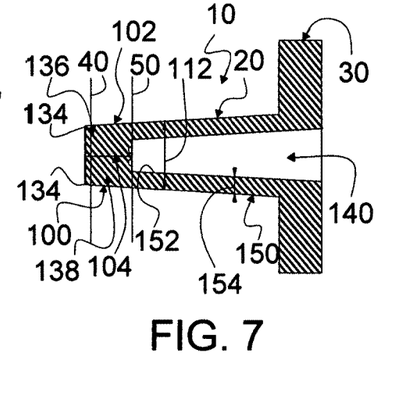
FIG. 7 is a longitudinal cross section of the valve part seen in FIG. 1.
Figure 7A:
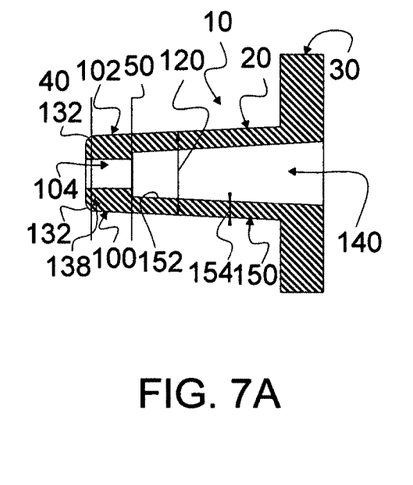
FIG. 7A is a longitudinal cross section of the valve part seen in FIG. 7 rotated ninety degrees.

As seen in FIG. 1A, proximal from a distal end 35, a first reference orthogonal plane 40 is disposed to provide a cross reference definition. A second reference orthogonal dissecting plane 50 is disposed proximally from plane 40 to provide a second plane of definition. Plane 40 is disposed to define a distal end of a valve core 100 (details of which are not seen in FIG. 1A, but are seen in FIGS. 7 and 7A). Valve core 100 comprises a slit valve 102 formed by a planar slit 104 which is opened, forming a fluid pathway, by radial compression when inserted into a tapered female luer fitting (see FIGS. 10 and 10A).

Plane 50, as seen in FIGS. 7 and 7A, is disposed at the proximal end of valve core 100. Body 20, being asymmetric, is seen to be smaller in cross section in FIG. 7, which depicts a view about the minor axis 112 of the ellipse, than in FIG. 7A which depicts a view about the major axis 120 of the asymmetric body 20. Each axis varies in length along a horizontal axis of part 10 as defined by taper of a fitting into which part 10 is displaced to open valve 102.

As seen in FIG. 7A, valve core 100 comprises beveled edges, commonly referenced by number 132, distally disposed relative to plane 40. It should be noted, as seen in FIG. 7, that valve core 100 comprises a pair of sharp edges 134. The purposes for contour of edges 132 are explained in detail hereafter. As seen in FIG. 7, slit 104 forms a pair of lips 136 and 138.

Figure 7B:
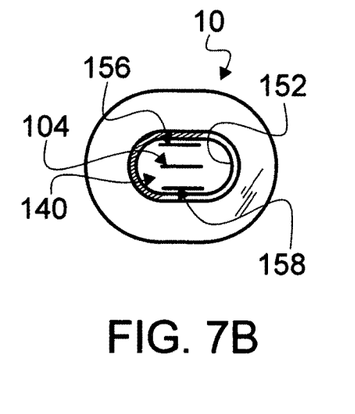
FIG. 7B is a proximal elevation of the valve part seen in FIG. 7.

Valve core 100 and body 20 combine to form a blind hole 140 which is also asymmetrically dimensioned as seen in FIGS. 7, 7A and 7B. Radial dimensions of hole 140 is defined by an exterior surface 150 of body 20, an interior surface 152 and wall thickness 154 (see FIGS. 7 and 7A). Exterior surface 150 is dimensioned to have an exactly comparable circumference to an associated tapered fitting into which part 10 is inserted along the entire length of insertion. Wall thickness 154 is constant, the measurement of which is determined by dimensional limitations of the selected tapered fitting, as disclosed in detail hereafter.

Attention is drawn to a pair of blind slits 156 and 158 (see FIGS. 7 and 7B), proximal ends of which each communicate with hole 140. The purpose and function of slits 156 and 158 are fully disclosed hereafter.

Figure 2:
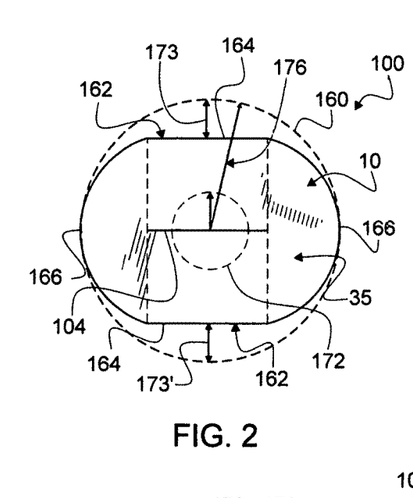
FIG. 2 is a cross section at a most distal end of the embodiment seen in FIG. 1 with a dashed line circle indicating circumference of inner surface of an associated female luer fitting when the valve is fully inserted therein.
Figure 3:
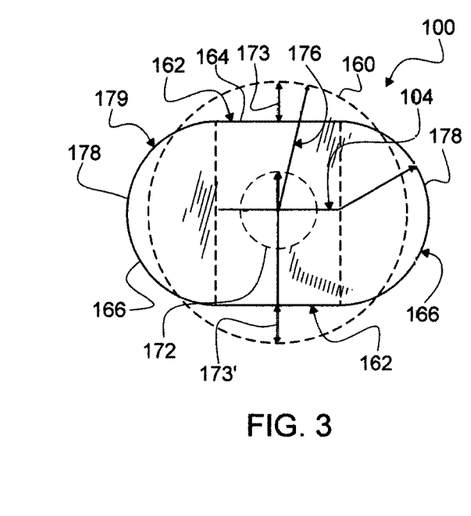
FIG. 3 is a cross section of the embodiment seen in FIG. 1, at a site of a most distal plane as seen in FIG. 1A, where circumference and area dimensions of the valve exactly correspond to similar internal dimensions of an inner surface of an associated female luer fitting (shown by a dashed line circle) into which the valve is fully inserted.

Reference is now made to FIGS. 2-5 wherein portions of valve core 100 and body 20 are seen in cross section. In FIG. 2, dashed line 160 represents the cross sectional circumferential dimension of a luer fitting into which part 10 is fully inserted. Solid line 162 represents the cross sectional circumferential dimension of part 10 at face 35. Note that line 162 is totally bounded by line 160. In this manner, ISO insertion size requirements are met. In FIG. 3, Solid line 162 is seen to comprise a pair of flat components (numbered 162 and 164) and two semicircular components (commonly numbered 166).

A planar cross section of the most distal portion of valve core 100, which meets circumference and area requirements for a fitting according to the instant invention, is seen in FIG. 3. At this site, a slit 104 which can be compressed to open to a substantially circular geometry (indicated by dashed line 172) is seen centrally disposed relative to circle 160. A radius of such a circle 172, formed by compression about slit 104, is hereafter referenced by "r" and by radius 173. As such, length of line 174, which is width of slit 104, is mathematically it $\pi^*r$ and area of circle 172 is $\pi^*r^2$. If a radius 176 of an associated female fitting at the site is denoted by "R", the circumference of the fitting (dashed line circle 160) is $\pi^*R$ and the area of the fitting thereat is it $\pi^*R^2$. Thus, the area of mass of an inserted valve 100, at the site, should be $\pi^*R^2-\pi^*r^2$, which describes the area of the fitting less the area of an opened pathway.

Note that, if line 164 is equal in length to width of slit 104 and is offset a distance of "r" from dotted line 160 (fitting circumference), as indicated by double arrow (numbered 173' due to length equivalence with line 173), and semicircular arcs 178 are affixed top and bottom to lines 164, as seen in FIG. 3, to form an asymmetric planar segment 179 of valve core 100 at the site, the combined length of pairs of lines 162, 164 and 178 is $2\pi^*r+2\pi^*(R-r)$ which equals $2\pi^*R$. Thus, the circumference of valve core 100 at the site is equal to the circumference of dashed line 160 or the fitting at the site. Such is true along the length of valve core 100.

Also, the area of valve core 100 at the site is $\pi^*r^*2\pi(R-r)+\pi^*(R-r)^2$ which reduces to $\pi^*R^2-\pi^*r^2$ (which is the fitting area less the formed hole area). Such circumferential and area relationships exist all along body 20 when fully inserted into an associated fitting. For these reasons, valve part 10 is the preferred embodiment.

Figure 4:
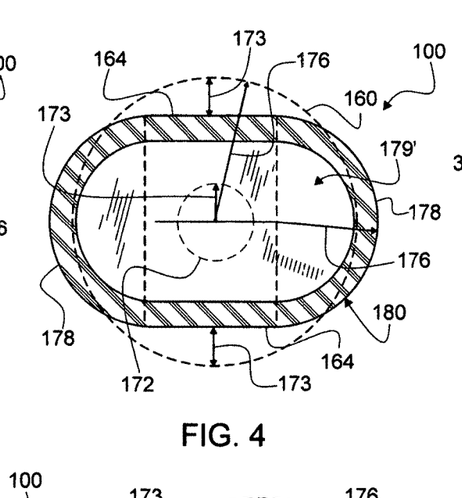
FIG. 4, similar to FIG. 3, is a cross section of the embodiment seen in FIG. 1, but at a site of the most proximal plane seen in FIG. 1A, where circumference and area dimensions of the valve exactly correspond to similar internal dimensions of an inner surface of an associated female luer fitting into which the valve is fully inserted.
Figure 5:
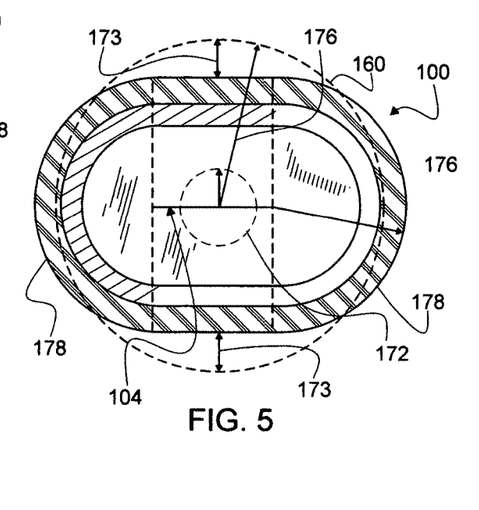
FIG. 5, similar to FIGS. 3 and 4, is a cross section of the embodiment seen in FIG. 1 at a site at a proximal end of an associated valve body, just distal from an anchor ring (seen in FIGS. 1 and 1A), where external; circumference and area dimensions of the valve exactly correspond to similar internal dimensions of an inner surface of an associated female luer fitting into which the valve is fully inserted.

FIG. 4 is a cross section at the proximal end 179' of valve 100. At this plane of reference, a preferable constant wall thickness skirt 180 extends proximally therefrom. Skirt 180 has the same exterior tapered dimensions as disclosed for valve 100. Thickness of skirt 180 is dependent upon material strength characteristics used in valve 10 manufacture. FIG. 5 is a cross section of valve part 10 just distal from anchor ring 30.

Valve Part 10'

Figure 6:
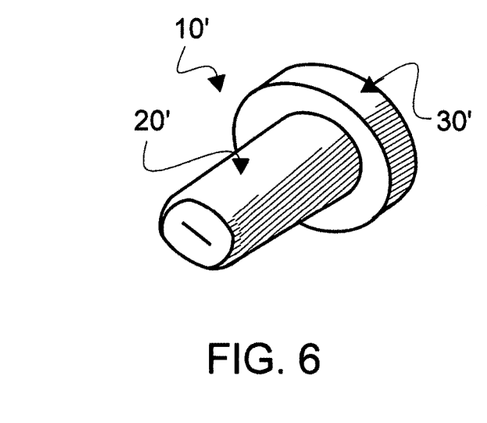
FIG. 6 is a perspective of another embodiment of an elliptical asymmetric valve part which is compressively opened according to the instant invention, the valve part being preferably molded from incompressible, elastic material.
Figure 6A:
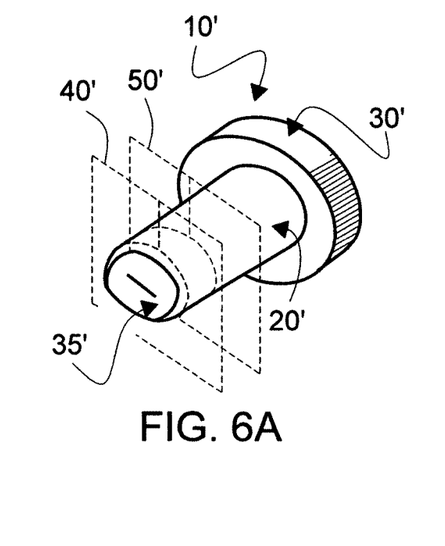
FIG. 6A is a perspective of the valve part seen in FIG. 6 with shading removed for a clearer view of planes disposed to identify crosscuts of the valve part at predetermined sites.

Reference is now made to FIGS. 6 and 6A wherein an asymmetric valve part 10' is seen. As seen in FIG. 6, valve part 10' comprises two sections, an asymmetric, tapered body 20' and a proximally disposed asymmetric anchor ring 30'.

As seen in FIG. 6A, proximal to a distal end 35', a first reference orthogonal plane 40' is disposed to provide a cross reference definition. A second reference orthogonal dissecting plane 50' is disposed proximally from plane 40' to provide a second plane of definition. Plane 40' is disposed to define a distal end of a valve core 100' (details of which are not seen in FIG. 6A, but are similar to that seen in FIGS. 8 and 8A). Valve core 100' employs an elliptically shaped body 20' rather than body 20 seen in FIG. 1. Valve part 10' and resulting uses for such are disclosed in detail in Thorne 257. Inclusion of disclosure of valve part 10' herein provides a broadened perspective of devices which are a part of the instant invention. Though valve part 10' can be made into an effective male luer valve, valve part 10 is preferred over valve part 10' because of the ability to manufacture valve part 10 with exact dimensions of a female tapered fitting.

Valve Insert Support 200

Figure 8:
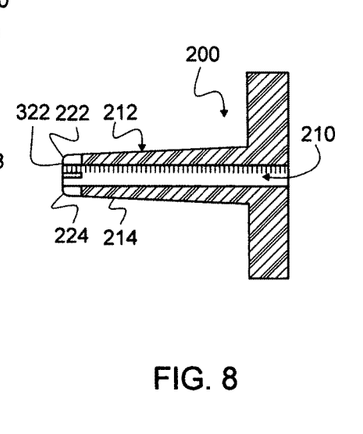
FIG. 8 is a cross section of an insertion support which is an integral part of a tapered fitting valve made according to the present invention.
Figure 8A:
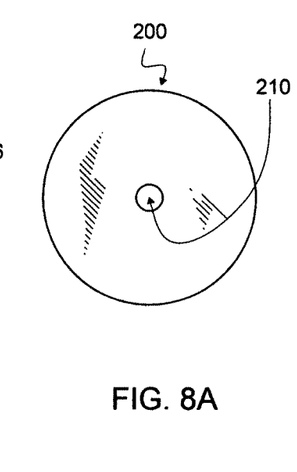
FIG. 8A is an elevation of the proximal face of the insertion support seen in FIG. 8.
Figure 8B:
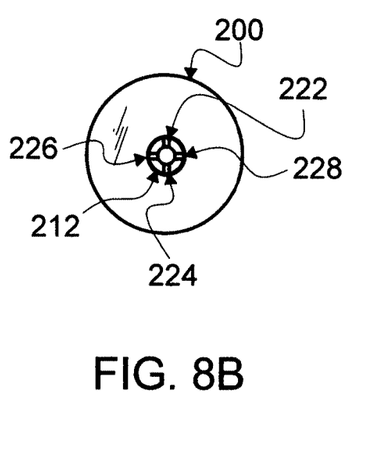
FIG. 8B is a distal elevation of the insertion support seen in FIG. 8.

A valve insert support 200 is seen in FIGS. 8 and 8A. Support 200 basically has three functions. First, support 200 provides a fluid communicating flow pathway 210 for fluid communication to valve core 100 once support 200 is inserted into a valve part, such as part 10 (see FIGS. 9 and 9A). Second, support 200, once inserted, provides physical support for valve part 10 when both part 10 and support 200 are inserted into an associated fitting. It should be noted that valve part 10 is generally made from material which is subject to deformation for which such support is required. Third, support 200 comprises an insertion stem 212, which comprises an elongated, tapered circular structure 214 which is sized and shaped to reform that portion of body 20 (see FIGS. 9 and 9A) into which stem 212 is inserted from an asymmetric to a circular (i.e. to match structure of an associated female tapered fitting). Valve support 200 has yet one other very important function. At a distal end 222, where valve support 200 interfaces with valve core 100, valve stem 212 comprises a beveled end 224, which provides a reduction in stress about surface 152 (see FIG. 7) where stem 212 and valve core 100 merge and a plurality of notches (numbered 222 and 224 in FIG. 8), the purpose for which is disclosed in detail hereafter.

Valve Assembly 300

Figure 9:
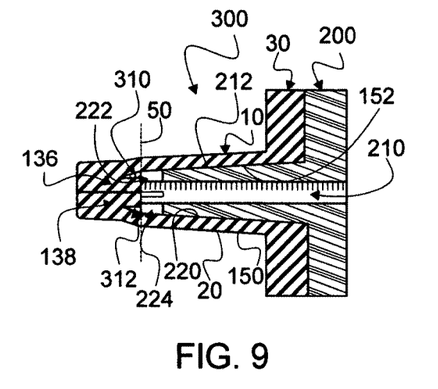
FIG. 9 is a cross section of the insertion support seen in FIG. 8 fully inserted, in a first rotational orientation, into the valve part seen in FIG. 7 to form an operational tapered fitting valve.
Figure 9A:
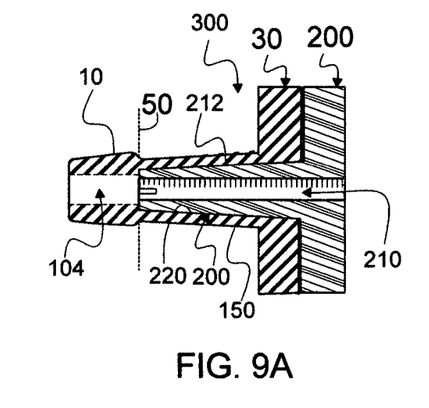
FIG. 9A is a cross section of the insertion support and valve part combination seen in FIG. 9, but rotated ninety degrees to a second orientation about a longitudinal axis.
Figure 9B:
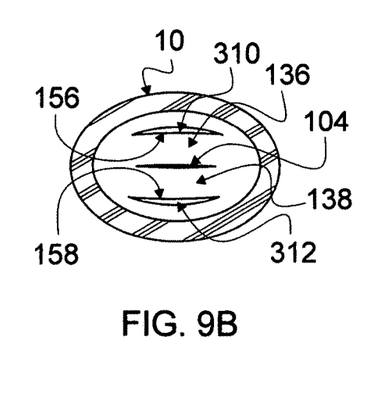
FIG. 9B is a cross section of the valve part, seen in FIG. 9, at a plane of intersection between the insertion support and valve part.

Reference is now made to FIGS. 9 and 9A wherein an assembled valve 300 is seen. Insertion of support 200 transforms a surrounding body portion 220 of valve part 10 from an asymmetric to a circular cross section. Support stem 212 is sized to engage the inner surface 152 of body portion 220 in a fluid tight relationship, as seen in FIGS. 9 and 9A.

When so assembled, and not inserted into a tapered fitting which opens valve core 100 by radially directed deformation, valve part 10 must remain closed to fluid flow in both directions. When upstream pressure is less than or equal to ambient surrounding pressure, valve core 100 performs as a conventional duckbill valve, remaining closed due to externally existing atmospheric pressure.

When upstream pressure is greater than ambient, it is well understood by those skilled in fluid dynamics that body portion 220 could expand and such expansion could part lips 136 and 138 with resultant valve opening. It should be noted that insertion of stem 212 into body 20 should result in a very tight fit about the minor axis 112 (see FIG. 3) of body 20 as seen in FIG. 9. However, full insertion of portion 220 also deforms body portion 220 about blind slits 156 and 158 to open cavities 310 and 312 (see FIGS. 9 and 9B)). Cavities 310 and 312 in cooperation with notches 222 and 224 (see FIGS. 9 and 8B), provide fluid pathways whereby upstream pressure is disposed about lips 136 and 138 to keep slit 104 and valve core 100 closed.

Such is not the case about major elliptical axis 120 (see FIG. 9A) near valve core 100. As seen in FIGS. 9 and 9A, insertion of stem 212 into body portion 220 also reforms wall 154 to be circular in cross section. This reformation about major axis 120 not only causes the associated section of body portion 220 to become circular but opens gaps along the major axis. Notches 226 and 228 (see FIG. 8B) communicate fluid and associated pressure along major axis 120 to aid in keeping valve core 100 closed.

Inserting Valves 300 and 300' into a Female Luer Fitting 400

Figure 10:
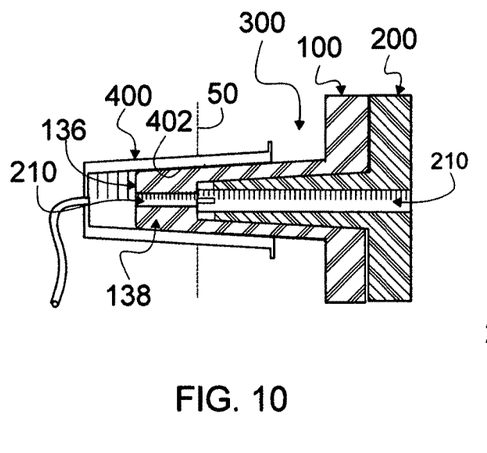
FIG. 10 is a cross section of an assembled tapered fitting valve, as seen in FIG. 9, inserted into a female luer fitting.
Figure 10A:
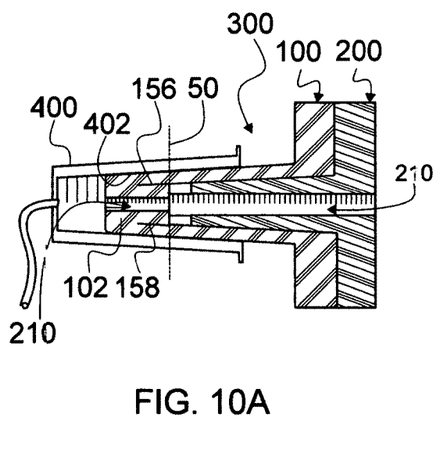
FIG. 10A is a cross section of the assembled tapered fitting valve inserted into a female luer fitting as seen in FIG. 10, but rotated ninety degrees about a longitudinal axis.
Figure 10B:
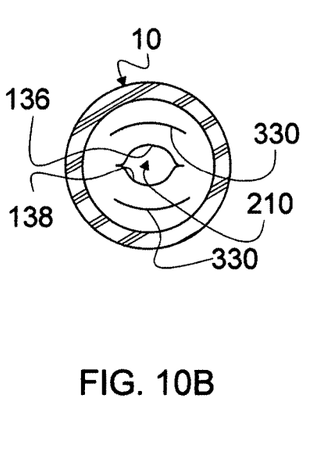
FIG. 10B is a cross section of the valve part, seen in FIG. 10, at a plane of intersection between the insertion support and valve part.

Reference is now made to FIGS. 10, 10A and 10B wherein a valve 300, as an example, is disposed within a female luer fitting 400. It should be noted that support 200 should be constrained to remain within valve part 10. However, in FIGS. 10 and 10A constraining members are not shown to reduce complicating structures and permit a clearer presentation of valve 300 performance within a female luer fitting. Examples of devices, each employing valve 300 with a constrained support 200, are provided hereafter.

Fitting 400 is a conventional tapered luer fitting having a circular cross section. As shown in FIGS. 10 and 10A, fitting 400 compresses valve core 100 to open a through hole (which is then a continuation of pathway 210 and, therefore, given the same number). A fluid tight fit is assured by constructing each linear circumferential segment of valve 300 to have the same circumference as the corresponding inner surface 402 of fitting 400. Exemplary geometry of pathway 210 which is opened between lips 136 and 138 is seen in FIG. 10B. Note, that associated parting of lips 136 and 138 also displaces blind slit groove pattern 330 away from pathway 210 to close cavities 310 and 312 (see FIG. 9B) Assurance of opening of pathway 210 thereat is provided by a medially disposed slit 104 along with closed cavities 310 and 312.

Male Adapter 600 Utilizing Elements of Valve Assembly 300 (i.e. Valve Part 10 and a Stem 212)

Figure 11:
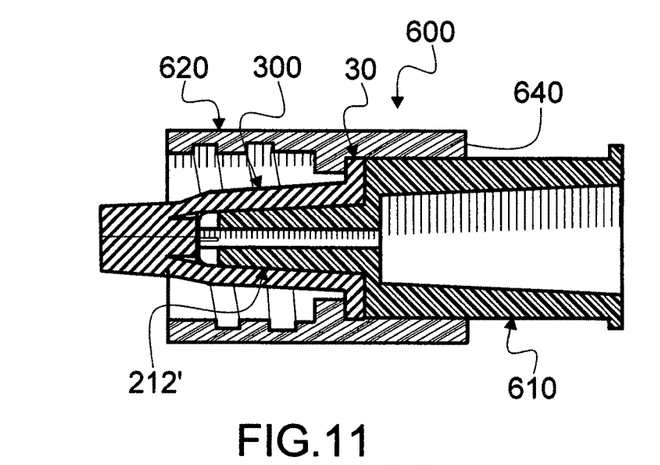
FIG. 11 is a cross section of a male adapter which utilizes parts of the assembled valve seen in FIG. 9.
Figure 11A:
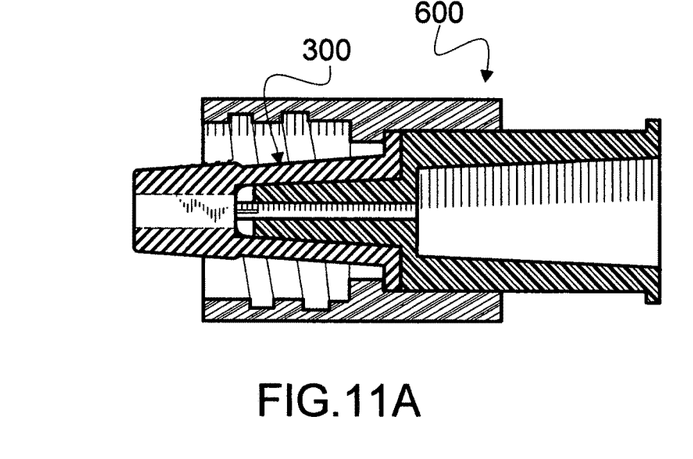
FIG. 11A is a cross section of the male adapter seen in FIG. 11, but rotated ninety degrees about a longitudinal axis.
Figure 12:
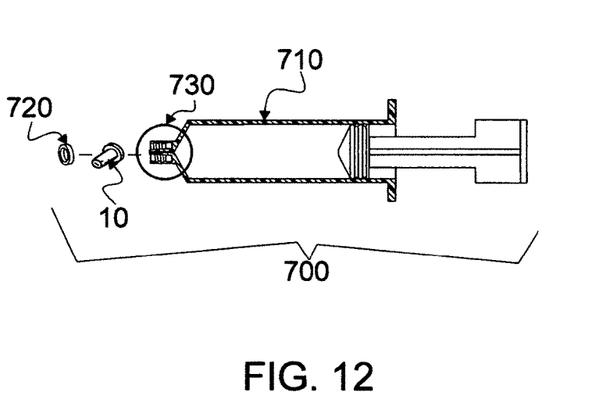
FIG. 12 is an exploded view of parts (with some items in cross section) which when assembled combine to provide a medical syringe with an integrally affixed male adapter.
Figure 13:
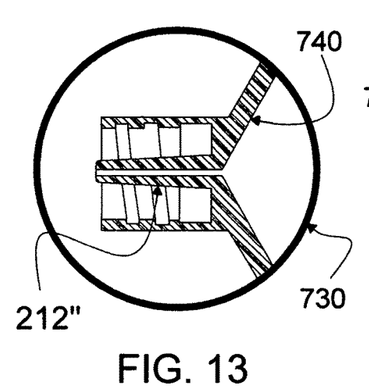
FIG. 13 is a magnified view of a circled portion of parts seen in FIG. 12.

An exemplary male adapter 600 which employs inventive elements of valve assembly 300' (see FIGS. 8 and 8A) is seen two rotational modes in FIGS. 11 and 11A. Adapter 600 comprises a valve part 10, a female luer fitting 610 which comprises an integrally molded stem 212' and a male luer lock fitting 620. Fittings 610 and 620 are joined along a common interface 640 by compression, adhesion, welding or threading (all commonly used in medical device construction) to capture anchor ring 30 (see FIG. 2). As such adapter 600 meets or exceeds all requirements for a self-closing fitting for medical applications.

Syringe Application for Valve Part 10

A syringe system 700 which employs a valve part 10 (and assembly 300) in place of a conventional male luer fitting is seen in various stages of assembly in FIGS. 12-15A. As seen in exploded format in FIG. 12, syringe system 700 comprises a conventional medical syringe 710 which is modified for interface with a valve part 10 and a retaining ring 720.

Figure 14:
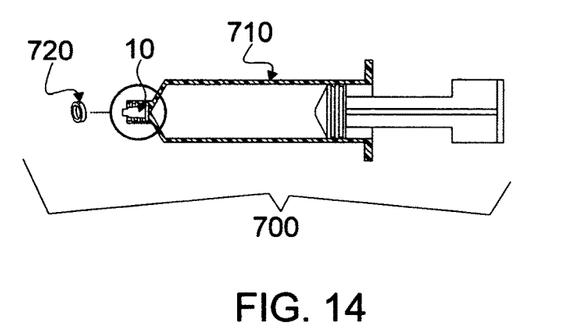
FIG. 14 is an exploded view of the parts seen in FIG. 12 with a first valve part affixed to a medical syringe which has an integrally molded insertion support.
Figure 14A:
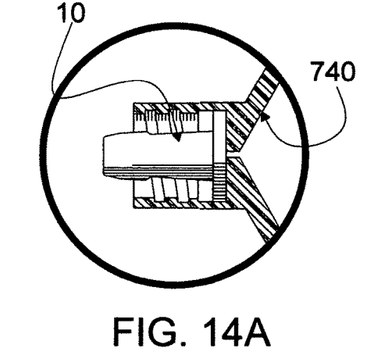
FIG. 14A is a magnified view of a circled portion of the parts seen in FIG. 14.
Figure 15:
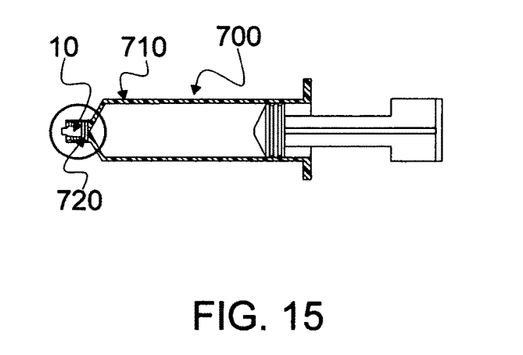
FIG. 15 is a side elevation, with portions in cross section, of a completely assembled medical syringe and integrally affixed male adapter.
Figure 15A:
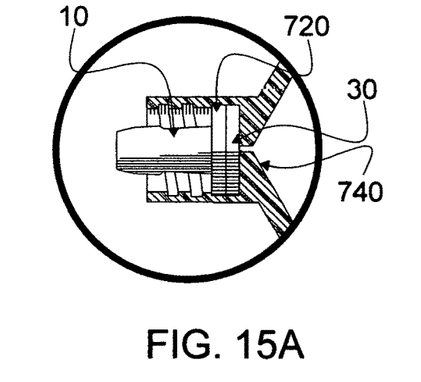
FIG. 15A is a magnified view of a circled portion of the parts seen in FIG. 15.

As seen in magnified circled reproduction 730 of a portion 740 of syringe 710, syringe 710 comprises an integrally molded stem 212" in place of a conventional male luer. Valve part 10 is affixed about stem 212" as seen in FIG. 14, but covered in FIG. 14A. As a final assembly step, retaining ring 720 is affixed to provide compressive, secure engagement as seen in FIGS. 15 and 15A.

Inventions disclosed herein may be embodied in other specific forms without departing from the spirit or essential characteristics thereof. The present embodiments are therefore to be considered in all respects as illustrative and not restrictive, the scope of the inventions being indicated by the appended claims rather than by the foregoing description, and all changes which come within the meaning and range of equivalency of the claims are therefore intended to be embraced therein.

What is claimed and desired to be secured by Letters Patent is:

1. A normally closed male valve which is opened by insertion into a circular female fitting having an interior surface defined by a predetermined taper and a plurality of contiguous fitting cross sections of variable radii, said valve comprising:
    a valve body, at a nose end of said valve, comprising incompressible but compliant, elastic material, said body comprising a planar slit which compressibly distorts to part and open said valve when inserted into the female fitting so as to form a pathway through the valve, said valve body comprising a tapered outer surface which encloses a plurality of contiguous valve body cross sections;
    each of said valve body cross sections comprising a rectangular middle section and two opposing semicircular sections, the rectangular middle section comprises a first pair of two opposite sides and a second pair of two opposite sides, each semicircular cross section being contiguously disposed against respective ones of the first pair of two opposite sides of said rectangular middle section, each of said semicircular sections comprising a diameter having the same length as the respective opposite side of the rectangular middle section and affixed thereto such that the outer surface is not discontinuous;
    each of said valve body cross sections comprising a planar, medially disposed linear portion of said slit which has a constant length and is orthogonally disposed relative to said two opposing sides;
    a pair of opposing surfaces defined by said slit which are aligned and joined when the valve body is undistorted to provide valve closure and are parted to provide a substantially circular through hole when the valve body is distorted by being fully inserted into the female fitting, the hole comprising a radius of predetermined size;
    a wall, disposed about said slit, comprising a plurality of wall cross sections along said slit, each wall section being of substantially constant thickness, the thickness being defined as the closest distance between said slit and said outer surface;
    wherein the second pair of two opposite sides of said rectangular middle section of each valve body cross section comprises a length substantially equal to the length of said slit portion of that cross section; and
    each of said valve body cross sections comprising dimensions which, when the valve body is fully inserted into the female fitting thereby associating the valve body cross sections with corresponding fitting cross sections, provide contact and closure between the interior surface of the female fitting and said outer surface of the valve body with each valve body cross section having the same circumference, an area of each valve body cross section being equal to an area of the associated fitting cross section less the area of the open pathway.

2. A normally closed male valve according to claim 1 further comprising an elongated hollow body affixed to and extended away from said valve body on a side opposite said nose end, said hollow body comprising an exterior surface which is shaped similarly to the valve body outer surface, but of an increasing dimension.

3. A normally closed male valve according to claim 2 wherein said hollow body comprises a medially disposed blind hole surrounded by a wall of constant thickness.

4. A normally closed male valve according to claim 3 wherein said valve comprises a tapered internal support which is displaced into said hollow body to provide structural support, said support comprising an elongated stem comprising a through hole of predetermined diameter and a tapered circular cross section which is displaced into said hollow body to reform the shape of said hollow body to a conforming, close fitting, circular cross section comparable to that of the tapered fitting.

5. A normally closed male valve according to claim 4 wherein said support further comprising notches at an end structure which contacts said valve body by which fluid and fluid pressure is communicated via said through hole against said valve body.

6. A normally closed male valve according to claim 5 wherein said valve body at an end away from the nose comprises a pair of blind slits which are displaced to an open state by insertion of said support into said hollow body and closed when said valve is inserted into the female fitting and when open provide a pathway for communicating fluid pressure into said open slits to maintain closure of said valve as an upstream fluid pressure is increased.

7. A normally closed male valve according to claim 3 wherein said valve comprises an enlarged anchor ring which is affixed to said hollow body at an end of the valve away from the nose end.

* * * * *